United States Patent [19]

Plotkin et al.

[11] 4,132,600

[45] Jan. 2, 1979

[54] ENZYMATIC NONINVASIVE METHOD FOR DETECTING CANCER

[75] Inventors: George M. Plotkin, Lynn; George Wolf, Lexington, both of Mass.

[73] Assignee: Massachusetts Institute of Technology, Cambridge, Mass.

[21] Appl. No.: 802,227

[22] Filed: Jun. 1, 1977

[51] Int. Cl.² ............................................. G01N 31/14
[52] U.S. Cl. ............................................. 195/103.5 R
[58] Field of Search ................................. 195/103.5 R

[56] References Cited

PUBLICATIONS

Weiser et al., Proceedings National Academy Science, vol. 73, pp. 1319–1322 (1976).

Porter et al., Nature, vol. 256, Aug. 21, 1975, pp. 648–650.

Primary Examiner—Lionel M. Shapiro
Attorney, Agent, or Firm—Arthur A. Smith, Jr.; David E. Brook

[57] ABSTRACT

An enzymatic noninvasive method for detecting cancer in mammalian tissue is disclosed. This method comprises incubating exfoliated cells from mammalian tissue suspected of containing cancerous cells, and assaying them for galactosyl transferase activity. The level of galactosyl transferase activity has been found to be significantly altered in cells from cancerous tissue as compared to the level in cells from normal tissue.

8 Claims, No Drawings

ENZYMATIC NONINVASIVE METHOD FOR DETECTING CANCER

BACKGROUND OF THE INVENTION

1. Field of the Invention

This invention is in the field of biochemistry and more specifically relates to an enzymatic noninvasive method for detecting cancer in mammalian tissue.

2. Description of the Prior Art

New methods for the diagnosis or prognosis of cancer, particularly in human beings, are clearly needed. In bladder cancer, for example, the most widely used method is histopathological and employs a cystoscope. Crystoscopy is costly, involves hospitalization of the patient, and is invasive which presents a certain risk of morbidity. A marker or test for bladder cancer which is not invasive is clearly desirable, particularly for low grade tumors which typically show no readily discernible symptoms.

Normal human bladder epithelium, sometimes called transitional epithelium, is 3–4 cell layers thick and consists of basal cells which are small and cubodial in shape, larger intermediate cells, and very large, highly differentiated cells at the outer, luminal surface. Hicks, The Mammalian Urinary Bladder, *Biol. Rev. Cambridge Phil. Soc.* 50, 215 (1975). The luminal membrane of these outer cells is unique: it consists of rigid plaques with a highly ordered substructure, separated by unstructured hinge regions. Chemically, this membrane has been found to consist mainly of lipid, with galactoside as one of the polar lipids and glycoprotein as the intrinsic protein embedded in the membrane. Histochemically, this membrane stained for the sugar components of the glycoprotein (Schiff's reagent) and for the negative charges of, presumably, sialic acid (Alcian Blue), the usual end-sugar of negatively charged glycoproteins.

When bladder cancer is induced in experimental animals, extensive changes occur in this surface membrane. The most productive animal model used is the Fischer rat, treated with 0.2% FANFT in the diet to give a high yield of exclusively bladder tumors. Cohen, Jacobs, Arai, Johansson, and Friedell; Early Lesions in Experimental Bladder Cancer: Experimental Design and Light Microscopic Findings, *Cancer Research* 36: 2508–2511 (1976).

It has been shown that after a 2–6 week treatment with the carcinogen, the normal, luminal surface is retained. Jacobs, Arai, Cohen and Friedell; Early Lesions in Experimental Bladder Cancer: Scanning Electron Microscopy of Cell Surface Markers, *Cancer Research* 36: 2512–2517 (1976). If at this time the carcinogen is withdrawn, no tumors ensue, although exfoliative cells are released as a result of hyperplasia, revealing the underlying surface of the intermediate cells, covered with uniform microvilli. After 8 weeks, microvilli of varying thickness and length appear. If the carcinogen is then withdrawn, hyperplasia continues with pleomorphic microvilli appearing on the luminal surface even after 50 weeks. If the carcinogen is fed 10 weeks or more, invasive carcinomas are formed, covered by pleomorphic microvilli. There is, therefore, a time-point of irreversibility in the carcinogenic process, coinciding with the appearance of the pleomorphic microvilli. Similar observations were made by others, in addition to the discovery of glycocalyx which covered the microvilli. Hicks and Wakefield; Membrane Changes During Urothelial Hyperplasia and Neoplasia, *Cancer Research* 36: 2502–2507 (1976).

A glycocalyx covering the microvilli of a luminal surface is also found in the intestinal and kidney mucosa. It is considered to be a network of enzymes covering the plasma membrane of the microvilli and consists of glycoprotein material, being labeled by sugar precursors (glucose, glucosamine, galactose, mannose). Ito, Structure and Function of the Glycocalyx; *Fed. Proc.* 28: 12 (1969).

It is clear, then, if only considered from a morphological and histochemical viewpoint, malignant transformation is accompanied by changes of the plasma membrane in the bladder epithelium involved. Glycoproteins are part of these membranes. Changes in specific glycoproteins of plasma members as a result of transformation have been well documented biochemically. Hynes, Cell Surface Proteins and Malignant Transformation. *Biochim. Biophy. Acta* 458: 73–107 (1976).

At the same time, recent evidence implicates the enzymes which are necessary in the synthesis of glycoproteins. In fact, Roseman proposed the involvement of cell-surface glycosyl transferases in contact inhibition of normal cell growth, and, of course, loss of such inhibition in transformed cells. Roseman, *Chem. Phys. Lipids*, 5: 270–297 (1970). Cell-surface galactosyl transferase has been detected in lymphocytes and other cells. Cacan, Verbert and Montreuil, New Evidence for Cell Surface Galactosyltransferase. *FEBS Letters* 63: 102–106 (1976). Porter and Bernacki, *Nature*, 256: 748–650 (1975). Recently, Weiser et al. found serum gal transferase in 58 patients with various types of carcinoma to increase almost 2-fold, and showed the presence of a gal transferase isoenzyme exclusively in the cancer patients. Weiser, Podolsky and Isselbacher, Cancer-associated Isoenzyme of Serum Galactosyltransferase. *Proc. Nat. Acad. Sci.* 73: 1319–1322 (1976). A 3–5 fold increase in this enzyme was detected in the serum of ovarian cancer patients. Galactosyl Transferase in Ovarian Cancer Patients, *Cancer Research* 36: 2096 (1976). Though the mechanism of the involvement of glycoproteins and glycosyl transferases in the malignant transformation is not understood, it is clear that there is an intimate connection between those compounds and enzymes, and the process of carcinogenesis.

DESCRIPTION OF THE INVENTION

This invention relates to the discovery that the level of a specific enzyme, galactosyl transferase, is significantly different in exfoliated cells from tissue containing cancerous cells than the level in comparable cells from normal tissue. Since such exfoliated cells are obtainable from body fluids, it is possible to perform an enzymatic, noninvasive test for cancer in mammalian tissue.

The method for detecting cancer in mammalian tissue comprises incubating exfoliated cells from tissue to be tested and assaying for the level of glycosyl transferase activity. In a preferred embodiment, this can be done by incubating the broken cells with an exogenous galactose acceptor, such as a modified glycoprotein, and a galactose-containing substrate, such as a nucleotide galactose sugar. The amount of galactose transferred in a given time under standard conditions to the acceptor can then be detected and is a measure of the level of galactosyl transferase activity. If this activity is significantly different from normal values, the organ is likely to contain cancerous tissue.

A convenient way to detect cancer of many organs is to incubate exfoliated cells from the suspected organ. In the case of the bladder, this can be done by centrifuging urine samples to obtain a pellet of exfoliated cells. The pellet can then be incubated and assayed for enzyme activity.

In a preferred assay technique, the exfoliated cells are collected from the appropriate body fluid, e.g., urine, by centrifugation, broken by sonication, and incubated with an exogenous galactose acceptor and with a galactose-containing substrate. Specific examples of suitable exogenous galactose acceptors are purified and desialated glycoproteins including: commercially obtained ovine submaxillary mucin (OSM), treated to remove sialic acid (e.g., with neuramidase); desialated, degalactosylated fetuin; desialated, bovine submaxillary mucin (BSM); the single sugar N-acetyl glucosamine and desialated OSM prebound to an insoluble matrix.

Convenient galactose-containing substrates are nucleotide galactose sugars such as uridine diphosphate galactose, which can be obtained as a radioactively labeled species from New England Nuclear. Standard scintillation counting techniques can then be used to detect the amount of sugar transferred from the nucleotide and bound to the galactose acceptor. Other galactose-containing substrates can be used, including lipid intermediates such as polyprenoid phosphate sugar.

Although the description herein is mainly directed to detection of bladder cancer, it is believed that other forms of cancer can be detected in human or other mammals by the techniques disclosed. For example, cancer of the genitourinary tract, the prostate, kidneys or trachea, etc., are believed detectable by the assay described herein. In addition to obtaining cells from urine (exfoliated bladder cells), they might also be obtained from the respiratory tract (exfoliated cells from bronchioles, bronchi and trachea found in mucus), from the buccal cavity (buccal scrapings and cells in sputum), from prostate secretion (exfoliated cells from prostate gland), and cells found in other body fluids, each revealing the presence of cancerous cells in the respective tissue.

The method of this invention, including the assay, is further described in detail by the following examples.

EXAMPLE 1

URIDINE 5'-DIPHOSPHATE GALACTOSE:GLYCOPROTEIN GALACTOSYL TRANSFERASE ACTIVITY IN EXFOLIATED BLADDER EPITHELIAL CELLS IN RATS FED N-[4-(5-NITRO-2-FURYL)-2-THIAZOLYL]FORMAMIDE

Groups of 4-week-old male Fischer rats were fed N-[4-(5-nitro-2-furyl)-2-thiazolyl]formamide (FANFT) at a dose of 0.2% by weight in their diet for 6, 8 and 30 weeks. FANFT is a known carcinogen. At the end of the carcinogen-feeding period, the rats were fed a normal diet until 50 weeks after beginning of treatment. At that time, they were placed in separate stainless steel metabolism cages, and their urines (about 2–5 ml) were collected through stainless steel funnels into flasks in ice over a period of 6 hours. The urines were centrifuged at 600 × g for 15 minutes to collect the exfoliated cells, which were then assayed for galactosyl transferase.

The assay used was performed as follows: Cells from about 5 ml urine were suspended in 200 µl 0.1 M MES buffer (pH 6.5) and sonicated for 5 seconds, with the sonicator set at 30 watts. The sonicate (20 µl) was incubated with 20 µl of 4% aqueous Triton X-100, 40 µl (containing 400 µg) of desialated ovine submaxillary mucin, 10 µl ATP solution (10 mg per ml) and 1 µC: of radioactively labeled uridine 5'-diphosphate galactose (UDP-[$^3$H]galactose) obtained from New England Nuclear Corporation, Boston, Mass. The incubation mixture was made 0.14 M with respect to manganese chloride with a final volume of 200 µl, and incubated at 37° C. The modified ovine submaxillary mucin was used to act as an exogenous galactose acceptor and was prepared from fresh ovine submaxillary glands obtained from a local slaughterhouse which had been purified and desialated according to the method of Murphy and Gottschalk. See Murphy, W. H. and Gottschalk. A., Studies on Mucoproteins. VII. The Linkage of the Prosthetic Group to Aspartic and Glutamic Acid Residues in Bovine Submaxillary Gland Mucoprotein; *Biochim. Biophy. Acta.* 52, 349 (1961).

A 20-µl sample was withdrawn at 30 minutes and another at 60 minutes. Each of these samples was mixed with 1 ml of 10% trichloroacetic acid and glycoprotein, was precipitated, filtered on a Millipore filter, washed with trichloroacetic acid, dried, transferred to a liquid scintillation vial and counted in a liquid scintillation counter. A further 20-µl sample was withdrawn from the incubation mixture for a protein determination according to the method of Lowry et al. See Lowry, O. H., Rosenbrough, N. S., Farr, A. L. and Randall, R. J.; Protein Measurement with the Folin Phenol Reagent; *J. Biol. Chem.* 193, 265 (1951). The amount of radioactive galactose transferred to glycoprotein in 30 and 60 minutes per ml urine or per mg protein indicated the activity of the galactosyl transferase.

A heavy mass of exfoliated cells was found in the urines of the rats which had been fed FANFT for 30 weeks compared to the mass of cells in the urines from normal rats. After centrifugation, the soluble supernatant fraction of urine contained no detectable galactosyl transferase either from treated or normal rats. On the other hand, upon sonication of the pellet of the exfoliated cells obtained after centrifugation, a many-fold higher than normal level of galactosyl transferase activity was found in the sonicate of the carcinogen-treated rats. The results are presented in Table 1.

TABLE I.

| Type of rat | Rat no. | Protein in sonicate (µg/20 µl) | Enzymatic activity[2] (dpm/20 µl sonicate) | | Specific enzymatic activity[b] (dpm/mg protein/60 min) |
|---|---|---|---|---|---|
| | | | in 30 min | in 60 min | |
| Normal | 1 | 58 | 360 | 756 | 13,030 |
| | 2 | 26 | 327 | 761 | 29,270 |
| | 3 | 30 | 390 | 708 | 23,600 |
| | 4[c] | 34 | — | 840 | 27,000 |
| | | | | | 23,255 ± 3,592[d] |
| Hyperplastic (fed FANFT for 6 weeks) | 1 | 29 | 364 | 820 | 28,275 |
| | 2 | 37 | 564 | 983 | 26,567 |

TABLE I.-continued

| Type of rat | Rat no. | Protein in sonicate ($\mu$g/20 $\mu$l) | Enzymatic activity[2] (dpm/20 $\mu$l sonicate) | | Specific enzymatic activity[b] (dpm/mg protein/60 min) |
|---|---|---|---|---|---|
| | | | in 30 min | in 60 min | |
| | 3 | 26 | 480 | 1,083 | 41,653 |
| | 4 | 37 | 401 | 496 | 13,405 |
| | 5[c] | 25 | — | 840 | 33,600 |
| | | | | | 28,700 ± 4,582[d] |
| Hyperplastic (fed FANFT for 8 weeks) | 1 | 37 | 450 | 639 | 17,270 |
| | 2 | 22 | 538 | 768 | 34,910 |
| | 3 | 12 | 540 | 864 | 69,120 |
| | 4 | 20 | 645 | 582 | 29,100 |
| | 5[c] | 67 | — | 1,380 | 20,700 |
| | | | | | 34,220 ± 9,273[d] |
| Tumor bearing[e] | 1 | 124 | 21,000 | 41,000 | 330,650 |
| | 2 | 176 | 22,200 | 42,900 | 243,750 |
| | 3 | 232 | 15,975 | 32,700 | 140,950 |
| | 4 | 232 | 48,600 | 83,400 | 359,480 |
| | 5[c] | 400 | — | 41,400 | 103,500 |
| | | | | | 235,666 ± 50,497[d] |

[a]Expressed as [$^3$H]galactose incorporated into OSM per incubation of 1 $\mu$Ci of UDP-[$^3$H]galactose (specific activity, 14.6 mCi/$\mu$mole).
[b]Expressed as [$^3$H]galactose incorporated into OSM per mg protein incubated.
[c]These samples were taken from a different experiment, in which the urines were collected 2 weeks earlier.
[d]Mean ± S.E.M.
[e]Colorimetric assay for hemoglobin-CO at 570 nm showed no detectable hemoglobin in any of these samples; there was thus no hematuria.

The higher than normal level of galactosyl transferase activity found in the pellet of exfoliated cells for the carcinogen-treated rats was not merely caused by the presence of a much larger number of cells in the urine of the treated rats. The specific activity of enzyme from the cells of carcinogen-treated rats showed a greater than 10-fold increase over that from normal cells. Statistically, the difference was significant at the level of $p < 0.0025$.

Cells from the rats with hyperplastic bladders resulting from ingestion of FANFT for 6 or 8 weeks did not have the remarkable increase in enzyme activity found in the cells of rats treated with FANFT for 30 weeks even though their hyperplastic bladders were clearly abnormal. In fact, the increased enzyme activity in the 6- or 8-week-treated animals was not statistically significant compared to normal. The difference in activity between the 6- or 8-week-treated rats and the 30-week-treated ones was significant at the level of $p < 0.0025$.

Urine samples were collected again from the same presumably tumor-bearing rats 3 weeks later, and there was clear evidence of hematuria. This phenomenon, together with exfoliation, indicated for certain that the rats were tumor-bearing. See Jacobs, J. B., Arai, M., Cohen, S. M. and Friedell, G. H.; Light and Scanning Electron Microscopy of Exfoliated Bladder Epithelial Cells in Rats Fed N-[4-(5-nitro-2-furyl)-2-thiazolyl]formamide, J. Nat. Cancer Inst. 57, 63 (1976b).

In order to obtain a meaningful specific enzymatic activity value for cells from the hematuric urines, a way had to be found to correct for the large amount of protein from the blood clot mixed with the cell pellet upon centrifugation. This correction was made by adding increasing amounts of rat blood to the supernatant fraction of centrifuged rat urine and by allowing a clot to form over 6 hours while the urines were kept cold in ice. A hemaglobin assay was then done on the precipitates and correlated with a protein assay, giving a correction curve. From this, the approximate amount of protein contributed by the blood clot in the hematuric urines to the protein of the exfoliated cells could be estimated, by measuring the hemaglobin mixed with the cells of the hematuric urines and using the correction curve to determine the protein. This amount of protein was subtracted from the total urinary protein, thus giving a corrected protein value and corrected specific enzymatic activity. Again, the specific enzymatic activity of galactosyl transferase from cells of hematuric rats bearing bladder tumors was over 7 times that from cells of normal rats. The results are illustrated in Table II.

TABLE II

| Type of rat | Rat no. | Protein in sonicate | Hemoglobin in sonicate | Protein in sonicate corrected | Enzymatic activity[a] | | Specific enzymatic activity | Specific enzymatic activity corrected |
|---|---|---|---|---|---|---|---|---|
| | | ($\mu$g/20 $\mu$l) | (OD/20 $\mu$l) | ($\mu$g/20 $\mu$l) | in 30 min | in 60 min | | |
| | | | | | (dpm/20 $\mu$l sonicate) | | (dpm/mg protein/60 min) | |
| Normal | 1 | 70 | 0 | 70 | 484 | 1,056 | 15,085 | 15,085 |
| | 2 | 32 | 0 | 32 | 549 | 1,106 | 34,562 | 34,562 |
| | 3[c] | 2,400 | 0.70 | 780 | 3,730 | 5,546 | 2,310 | 7,110 |
| | | | | | | | | 24,823 ± 9,746[d] |
| Tumor bearing[e] | 1 | 460 | 0.15 | 110 | 7,200 | 12,453 | 27,071 | 113,200 |
| | 2 | 640 | 0.30 | 40 | 5,660 | 9,483 | 14,817 | 238,000 |
| | 3 | 352 | 0.10 | 152 | 20,380 | 44,290 | 125,823 | 291,380 |
| | 4 | 1,000 | 0.10 | 88 | 39,810 | 60,820 | 60,820 | 76,025 |

TABLE II-continued

| Type of rat | Rat no. | Protein in sonicate | Hemoglobin in sonicate | Protein in sonicate corrected | Enzymatic activity[a] | | Specific enzymatic activity | Specific enzymatic activity corrected |
|---|---|---|---|---|---|---|---|---|
| | | | | | in 30 min | in 60 min | | |
| | | | | | | | | 179,651 ± 50,826[d] |

[a]Expressed as [³H]galactose incorporated into OSM per incubation of 1 μCi of UDP-[³H]galactose (specific activity, 14.6 mCi/μmole).
[b]Expressed as [³H]galactose incorporated into OSM per mg protein incubated.
[c]One-half milliliter of normal rat blood was added to this urine.
[d]Mean ± S.E.M.
[e]These urines all contained blood.

It is known that erythroctyes show galactosyl transferase activity adsorbed onto their cell surface. See Podolsky, D. C., Weiser, M. M., LaMont, J. T. and Isselbacher, K. J.; Galactosyl Transferase and Concanavalin A Agglutination of Cells, *Proc. Natl. Acad. Sci. U.S.A.*, 71, 904 (1974). The possibility existed, therefore, that some of the erythrocytes in the blood clot found mixed with the hematuric urines may have carried down some galactosyl transferase. To exclude this possibility, an amount of normal blood was added to the urine of one of the normal control rats (Table II, Rat No. 3), such that the hemaglobin value would be more than twice the highest hemoglobin value of the hematuric tumor-bearing rats. Even though the total enzyme activity after adding the blood to the urine was greater than that of the urine without added blood, it remained much les than that of the tumor-bearing rats.

EXAMPLE 2
COMPARATIVE GLYCOPROTEIN GALACTOSYL TRANSFERASE ACTIVITIES

Using the standard incubation and assay described in Example 1, the level of glycoprotein galactosyl transferase activity was determined for cells or urine from a number of sources.

A large number of samples of human urine, both male and female, from healthy, normal volunteers, was assayed, and without exception, the gal transferase activity in exfoliated cells was virtually zero. After centrifugation to remove the cells, the supernatant of normal urines was found to contain some activity. The human soluble urinary enzyme incorporated 1600 dpm [³H]galactose/60 min/80 μl urine, when using 1 μCi UDP-[³H]galactose as substrate (specific activity, 14.6 mCi/umole). [³H]galactose transfer was proportional with time.

Urine from normal Sprague-Dawley rats, both soluble fraction and exfoliated cell pellet, showed almost no activity.

Normal rat bladder, when sonicated and incubated, had an enzyme activity of 700 dpm/60 min/rat in the standard assay.

EXAMPLE 3
URIDINE 5'-DIPHOSPHATE GALACTOSE:GLYCOPROTEIN GALACTOSYL TRANSFERASE ACTIVITY IN HUMAN URINE SAMPLES

The assay procedures of Example 1 were used to detect enzyme activity in the soluble fraction and exfoliated cells obtained as a pellet upon centrifugation of samples of urine from human beings. Table III presents the results. It can be seen that the studies were carried out "blind" in that in each case the results of the enzyme assay pre-date the results of the histology-cytology report which indicated whether tumor growth had recurred or not, or whether the cells were due to an inflammatory disease.

Case 1 compares the cells and supernatant fluid from urine of normal, healthy volunteers to a patient with transitional cell carcinoma. It is clear that, both per ml urine and per mg protein, cells from the cancer patient show many times the activity of the normal.

Case 2 shows very high activity in the cells from a recurrent tumor, both in soluble and cells obtained by a cystoscopic bladder wash.

Case 3 shows that a carcinoma grade II shows activity, but slightly less than the recurrent tumor of Case 2.

Case 4 illustrates the application of this assay as a control: no activity was detectable, and 7 days after this result was obtained, the cytology report showed no tumor.

Case 5 again shows activity in a grade II tumor.

Case 6 is noteworthy, since the exfoliated cells show some, but not a very high level of activity. Six days after the assay, this was diagnosed as a grade I (low invasiveness) tumor.

TABLE III

CASE 1: Male, 49 years old.
Papillary transitional cell carcinoma removed 6/11/75.
Cytology negative in 3–4 cystoscopies since then. Urine removed (4 ml) during cystoscopy 12/29/76.
Human Urine

| Fraction | Radioactivity transferred as H³ galactose to glycoprotein in | | CPM/ml urine | CPM/mg creatinine | CPM/mg protein |
|---|---|---|---|---|---|
| | 30 min (CPM) | 60 min (CPM) | | | |
| Normal[a] soluble | 249 | 540 | 54 | — | — |
| Patient soluble | 104 | 168 | 64 | — | — |
| Normal[a] Exfoliated cells | 70 | 74 | 7 | 5 | 2700 |
| Patient Exfoliated cells | 216 | 383 | 191 | 96 | 9575 |

[a]Normal urine was mixture of urines from healthy male volunteers

Assay done 12/29/76
Cytology reported 1/3/77: recurrence of papillary transitional cell carcinoma.

CASE 2: Male, 63 years old, tumor resection, irradiation treatment Bladder washing.

| | | | | | |
|---|---|---|---|---|---|
| Washing (soluble) | 381 | 801 | | | 11,125 |

TABLE III-continued

| | | | | |
|---|---|---|---|---|
| Washing (exfoliated cells) | 1399 | 2514 | | 12,570 |

Assay done 1/5/76.
Cytology reported 1/10/76: recurrence of tumor.
CASE 3: Bladder washings and urine from male, 71 years old.

| Fraction | Radioactivity transferred as $H^3$ galactose to glycoprotein in | | CPM/mg creatinine | CPM/mg protein |
|---|---|---|---|---|
| | 30 min (CPM) | 60 min (CPM) | | |
| exfoliated cells | 329 | 642 | 17.8 | 8000 |
| bladder washings | 141 | 240 | — | 7500 |

Assay performed: 1/11/77
Cytology/Pathology reported: 1/18/77: transitional cell carcinoma, grade II.

CASE 4: Bladder washings from female,

| Fraction | Radioactivity transferred as $H^3$ | | CPM/mg galactose to glycoprotein in | CPM/mg creatinine | protein |
|---|---|---|---|---|---|
| | 30 min (CPM) | 60 min (CPM) | | | |
| bladder washings | 0 | 0 | 0 | 0 | |

Assay done: 1/11/77
Cytology/Pathology reported: 1/18/77: acute inflammation, no tumor.

CASE 5: Bladder washings and urine from male, 74 years old.

| Fraction | Radioactivity transferred as $H^3$ galactose to glycoprotein in | | CPM/mg creatinine | CPM/mg protein |
|---|---|---|---|---|
| | 30 min (CPM) | 60 min (CPM) | | |
| exfoliated cells | 265 | 526 | 29.1 | 13,162 |
| bladder washings | 2269 | 3009 | — | 47,028 |

Assay done: 1/12/77
Cytology/Pathology reported: 1/18/77: transitional cell carcinoma, grade II.

CASE 6: Bladder washings and urine from male, 77 years old.

| Fraction | Radioactivity transferred as $H^3$ galactose to glycoprotein in | | CPM/mg creatinine | CPM/mg protein |
|---|---|---|---|---|
| | 30 min (CPM) | 60 min | | |
| exfoliated cells | 37 | 97 | 14.7 | 4875 |
| bladder washings | 286 | 573 | — | 28,7650 |

Assay done: 1/12/77
Cytology/Pathology reported: 1/18/77: transitional cell carcinoma, grade I.

It can be seen from the description above that the assay for galactosyl transferase activity in exfoliated cells is useful as a noninvasive test for cancer in tissue from mammals, including humans.

There are, of course, many variations to the specific steps, techniques, dosages, materials, etc., used in the work described herein. Additionally, there is evidence that the level of galactosyl transferase activity is decreased in exfoliated cells from trachea epithelium exposed to benzopyrene, so that the alteration in the level of gal transferase associated with an abnormal tissue condition appears as though it may be raised or lowered. All equivalents to the embodiments expressly described herein are intended to be encompassed within the following claims.

What is claimed is:

1. A method for detecting cancer in mammalian tissue comprising assaying exfoliated cells from said tissue for a significantly altered level of galactosyl transferase activitiy.

2. A method of claim 1 wherein said exfoliated cells are obtained noninvasively from body fluid.

3. An enzymatic, noninvasive test for cancer in the tissue of mammals, comprising:

a. incubating broken cells exfoliated from said tissue with an exogenous galactose acceptor and an exogenous galactose-containing substrate;
   b. determining the level of galactose transferase activity present in said tissue; and,
   c. comparing the level of galactose transferase activity to the level associated with non-cancerous tissue of the same type.

4. The test of claim 3 wherein said exogenous galactose acceptor comprises a glycoprotein.

5. The test of claim 4 wherein said glycoprotein is selected from desialated ovine submaxillary mucin, desialated degalactosylated fetuin, desialated, bovine submaxillary mucin, and N-acetyl glucosamine and desialated ovine submaxillary mucin bound to an insoluble matrix.

6. The test of claim 5 wherein said exogenous galactose-containing substrate comprises a nucleotide or lipid bound to galactose.

7. The test of claim 5 wherein said exogenous galactose-containing substrate comprises uridine 5'-diphosphate galactose.

8. The test of claim 7 wherein said exogenous galactose-containing substrate comprises desialated ovine submaxillary mucin.

* * * * *